(12) United States Patent
Pick et al.

(10) Patent No.: US 7,744,551 B2
(45) Date of Patent: Jun. 29, 2010

(54) TEMPERATURE REGULATED COMPRESSION BRACE

(75) Inventors: Erez Pick, Roslyn Heights, NY (US); Johan de Ruiter, Munich (DE); Hermann Otto Mayr, Munich (DE)

(73) Assignee: DJO, LLC, Vista, CA (US)

( * ) Notice: Subject to any disclaimer, the term of this patent is extended or adjusted under 35 U.S.C. 154(b) by 316 days.

(21) Appl. No.: 11/493,152

(22) Filed: Jul. 25, 2006

(65) Prior Publication Data

US 2007/0161932 A1 Jul. 12, 2007

Related U.S. Application Data

(60) Provisional application No. 60/702,365, filed on Jul. 25, 2005.

(51) Int. Cl.
*A61F 5/00* (2006.01)
(52) U.S. Cl. .................... 602/5; 602/14; 602/17
(58) Field of Classification Search ........... 602/1, 602/2, 5, 13, 14, 18, 19, 20, 23, 26
See application file for complete search history.

(56) References Cited

U.S. PATENT DOCUMENTS

| | | | |
|---|---|---|---|
| 5,230,335 A * | 7/1993 | Johnson et al. ............. 607/104 |
| 5,314,455 A | 5/1994 | Johnson, Jr. et al. |
| 5,626,557 A | 5/1997 | Mann |
| 5,632,725 A * | 5/1997 | Silver et al. .................. 602/26 |
| 5,641,322 A | 6/1997 | Silver et al. |
| 6,352,550 B1 * | 3/2002 | Gildersleeve et al. ....... 607/108 |
| 7,122,016 B1 * | 10/2006 | DeToro et al. ................. 602/26 |
| 2004/0153016 A1 * | 8/2004 | Salmon et al. ................. 602/16 |
| 2005/0187502 A1 * | 8/2005 | Krempel et al. ................. 602/5 |
| 2006/0200057 A1 * | 9/2006 | Sterling ......................... 602/5 |

FOREIGN PATENT DOCUMENTS

WO    WO 95/32690    12/1995

* cited by examiner

*Primary Examiner*—Patricia M Bianco
*Assistant Examiner*—Tarla R Patel
(74) *Attorney, Agent, or Firm*—Dickstein Shapiro LLP

(57) ABSTRACT

The systems and methods described herein include systems and methods for applying temperature regulated compression and support to certain injured portions of the human body. In particular, the systems and methods relate to a brace to be fitted around a joint of a human for applying therapeutic temperature regulated compression to the joint and having rigid supports disposed therein to provide support for the limb while a patient recuperates from surgery or other injury.

56 Claims, 9 Drawing Sheets

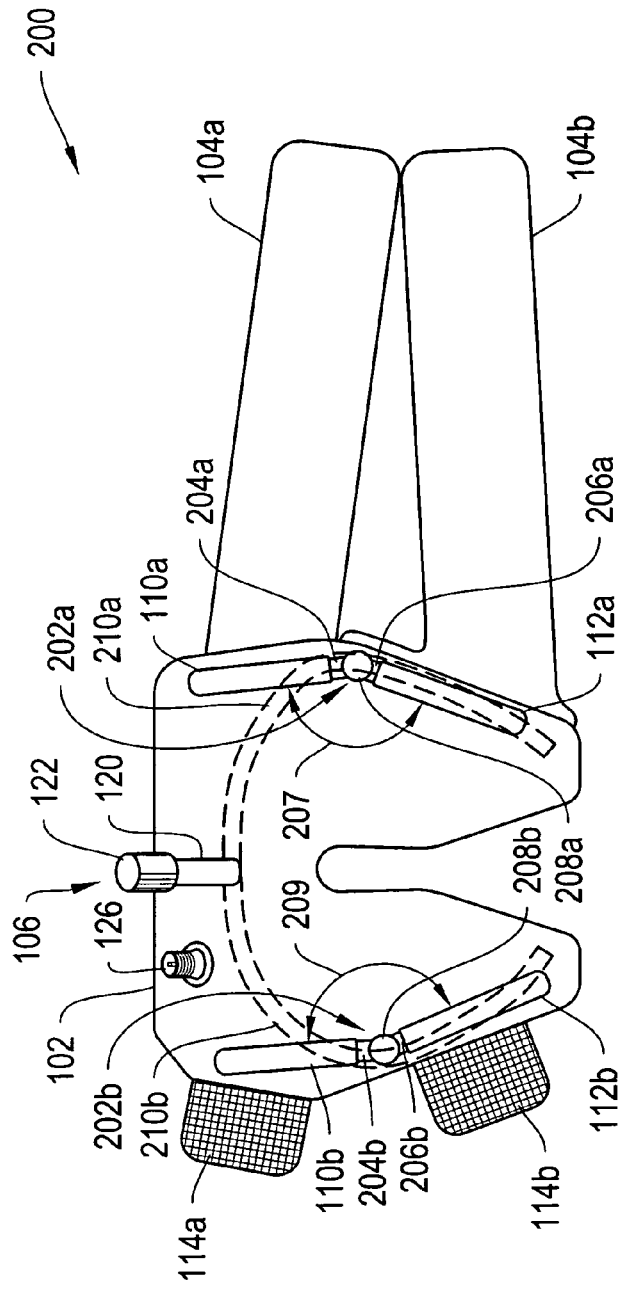
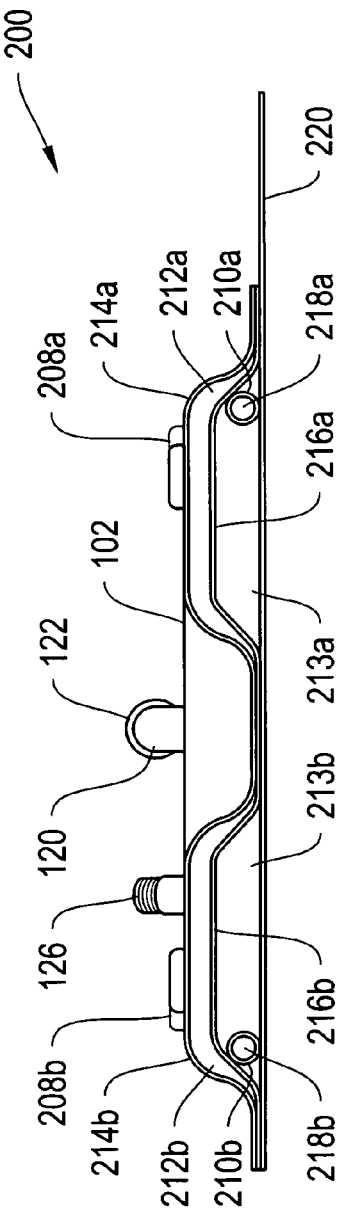
Figure 2A
Figure 2B

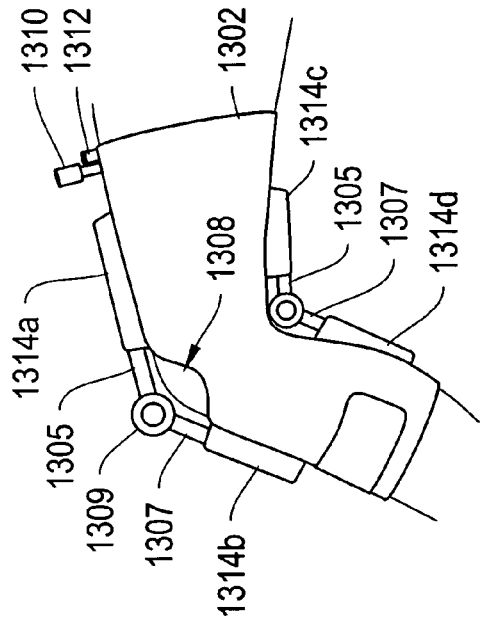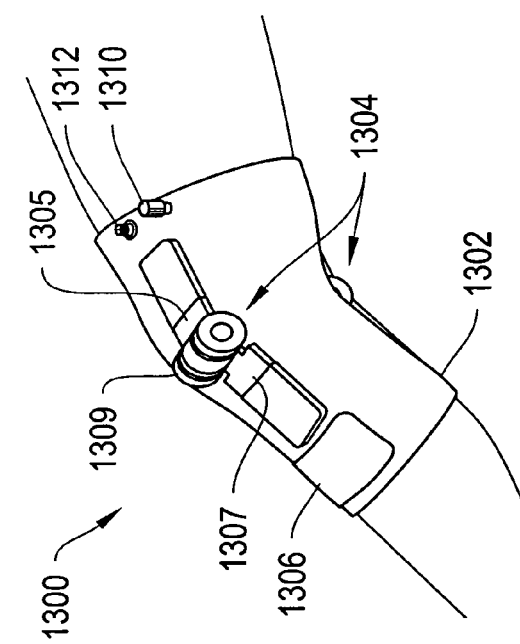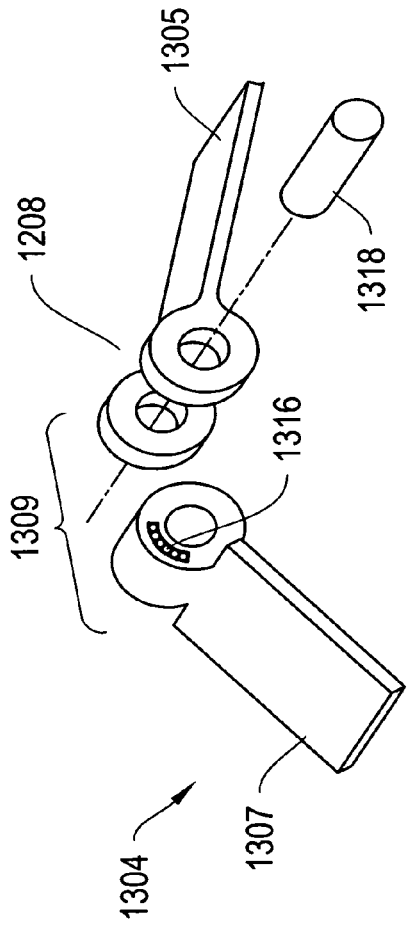

TEMPERATURE REGULATED COMPRESSION BRACE

CROSS REFERENCE TO RELATED APPLICATIONS

This application claims priority to and the benefit of U.S. Provisional Patent Application Ser. No. 60/702,365, filed on Jul. 25, 2005 and entitled "Heat and Cold Compression Device with Hinged Support," to Erez Pick et al., the entire contents of which are incorporated herein by reference.

BACKGROUND

After surgery to an injured joint such as the knee, compression and cold are applied to control the swelling and the commonly occurring hemarthrosis that causes pain and delays rehabilitation. Modalities for postoperative cold and compression traditionally have been applied separately—the compression most commonly by an elastic bandage wrapped around the injured body part, and the cold by a superimposed plastic bag filled with ice. While this approach is simple and can be economical, it has its own complications including minimal re-usability of the elastic bandage, short life span until the ice melts and non-uniform application of cold and compression due to gradual warming of the fluid in the vicinity of the patient and irregular distribution of ice in the bag. To address these problems, certain devices such as the Aircast CRYO/CUFF™ brace have been developed that apply compression and cold therapy in a unitary compression system.

Although these systems work quite well for applying compression and cold therapy to the injured body part, they are often not sufficiently rigid to support the limb when fully engaged by the patient. Thus, the patient may have more mobility and limb functionality than desired during recuperation. The patient is also more susceptible to re-injuries caused by joint hyper-extension and unnatural medial (inward) and lateral (outward) movement of the joint.

Accordingly, it is an object of the invention to provide a bracing system that offers both the therapeutic benefits of cold (or hot) therapy and compression along with bracing support to allow the patient to more naturally use the limb during recuperation.

SUMMARY OF THE INVENTION

The systems and methods described herein include systems and methods for applying temperature regulated compression and support to certain injured portions of the human body. In particular, the systems and methods relate to a brace to be fitted around a joint of a human and its use in applying therapeutic temperature regulated compression along with bracing support to the joint.

In one aspect, the invention contemplates a unitary, cryotherapy bracing system for a human limb that can be worn by the patient when carrying out intensive load-bearing activities during recuperation from surgery to the limb. In certain implementations, the system includes a flexible shell configured to be removably secured about a patient's limb near a joint, a fluid compartment formed within the flexible shell and configured with a fluid port for receiving external cooling or warming fluid for application to the area near the joint, and one or more rigid support members coupled to the flexible shell for bracing the joint.

In certain implementations the system is configured to fit to a human knee, ankle, wrist, elbow, shoulder, or spine. The system may also include at least one strap connected to the flexible shell and extending therefrom for removably securing the flexible shell about the limb. The flexible shell may include an aperture for receiving a portion of the joint. The system may also include a fluid port in fluid communication with the expandable fluid compartment for introducing fluid into the expandable fluid compartment.

In certain implementations the system includes one or more rigid members. For example, the system may include at least two rigid members disposed on the lateral and medial portions of the joint. The rigid member is made of any stiff or rigid material that can suitably support the human limb while being used in typical daily tasks, such as running, writing, throwing, and lifting. In certain embodiments the rigid members include at least one of metal, plastic or fiberglass. The system may include a pocket attached to the flexible shell for accommodating the rigid member. The rigid member may be removably disposed within the pocket.

The rigid member may also include a hinge coupled to it for allowing controlled movement of the joint. The rigid member may include a selectable hinge for adjusting the orientation of the rigid member. The selectable hinge may be configured to rotate within a range of degrees of freedom (e.g., from about 10° to about 15°). The hinge may also include a rachet mechanism. In certain embodiments the rigid member includes proximal and distal rigid members, and the selectable hinge is adapted to fix the proximal and distal rigid members at an angle with respect to each other that is less than 180°.

The fluid compartment may be formed from any substantially fluid impervious material for containing the temperature regulated fluid. In certain embodiments the fluid compartment is inflexible and is compressed against the limb by at least one strap. In other embodiments, the fluid compartment is flexible and adapted to compress the limb when fluid is placed therein. The fluid compartment is formed from a material capable of receiving and/or holding at least one of a high temperature fluid (e.g., above about 30° C.) such as hot water that may be commonly used in a hot pack, and a low temperature fluid (e.g., below about 10° C.) such as ice water. The expandable fluid compartment may also include a layer of insulation.

In certain embodiments, the systems include an output port in fluid communication with the fluid compartment for removing the temperature regulated fluid from the fluid compartment.

In certain embodiments, the systems include an outer compartment formed within the flexible shell and located near the fluid compartment. Air is introduced into the outer compartment such that the outer compartment expands and imparts compressive force to the joint. In certain embodiments, the brace includes a siphon disposed within the flexible shell and in fluid communication with the fluid port and the fluid compartment. Temperature regulated fluid may pass from the fluid port to the fluid compartment via the siphon.

In another aspect, a fluid reservoir is connected to the fluid port such that the temperature regulated fluid can be introduced from the fluid reservoir into the fluid compartment through the fluid port. The brace may include an air release valve to allow air to escape when the temperature regulated fluid is introduced into the fluid compartment. In one embodiment, the temperature regulated fluid is introduced into the expandable fluid compartment through a fluid port that may be in fluid communication with the expandable fluid compartment.

In another aspect, the invention relates to methods for applying temperature regulated compression and support to a joint. In certain embodiments the invention contemplates a method of bracing a patient's limb and includes the steps of applying a fluid-receiving compartment about the limb, applying at least one rigid member along at least one of lateral and medial sides of the limb, the rigid member being coupled to the fluid-receiving compartment, and inserting a temperature regulated fluid into the fluid-receiving compartment to compress the limb, while concomitantly bracing the limb by the at least one rigid member. In certain embodiments, the fluid-receiving compartment includes a fluid compartment disposed within a shell of a brace. In other embodiments, the fluid-receiving compartment includes a fluid compartment that is directly applied to the patient's limb.

In one implementation, the methods include applying a brace having a fluid compartment to the limb along with a rigid member that fits interoperationally about the limb with the fluid compartment and supports the limb. The method also includes the step of inputting temperature-controlled fluid into the fluid compartment, thereby expanding the brace to press it against the joint and exchange thermal and compressive energy with the joint. The method also includes the step of stabilizing the limb while the patient wears the brace and carries out daily activities such as walking, running, writing, throwing, and lifting. The rigid member may be configured to maintain the structure of the brace as the expandable fluid compartment expands.

In certain implementations, the methods are carried out using the system embodiments disclosed herein. In certain exemplary embodiments, the methods are carried out using a bracing system having a flexible shell, an expandable fluid compartment formed within the flexible shell and a rigid member coupled to the flexible shell. In alternative implementations, the methods are carried out using a bracing system with a rigid fluid compartment which is compressed against the limb by a strap. The methods may also include the steps of securing a compression system about a limb and introducing a temperature regulated fluid into the expandable fluid compartment through the fluid port. In certain embodiments, the methods include the step of locking one or more rigid members about the joint at a desired angle such that the one or more rigid member in combination with the lockable hinge impedes the joint from hyper-extending.

In certain embodiments the methods also include the step of adjusting the temperature or compressive effect of the bracing system, such as by removing the temperature regulated fluid from the expandable fluid compartment, switching cold and warm/hot fluid within the compartment, tightening the strap, or any other step to adjust the temperature of the fluid or level of compression applied to the limb. In one embodiment, the steps of introducing and removing the temperature regulated fluid from the expandable fluid compartment are carried out iteratively, thereby providing a continuous supply of temperature regulated fluid to a portion of the joint.

BRIEF DESCRIPTION OF THE DRAWINGS

The following figures depict certain illustrative embodiments of the invention in which like reference numerals refer to like elements. These depicted embodiments may not be drawn to scale and are to be understood as illustrative of the invention and not as limiting in any way.

FIGS. 2A and 2B depict alternate views of the temperature regulated compression brace shown in FIG. 1, according to an illustrative embodiment of the invention.

FIG. 10A depicts a perspective view of a temperature regulated compression brace as applied to a patient's knee, according to an illustrative embodiment of the invention.

FIG. 10B depicts a side view of a temperature regulated compression brace as applied to a patient's knee, according to an illustrative embodiment of the invention.

FIG. 10C depicts a three-dimensional view of a support system for a temperature regulated compression brace, according to an illustrative embodiment of the invention.

These and other aspects and embodiments of the systems and methods of the invention will be described more fully by referring to the figures provided.

DETAILED DESCRIPTION OF THE ILLUSTRATED EMBODIMENTS

The systems and methods described herein will now be described with reference to certain illustrative embodiments. However, the invention is not to be limited to these illustrated embodiments which are provided merely for the purpose of describing the illustrative systems and methods, and are not to be understood as limiting in any way. Although described below with reference to an embodiment that treats and braces a knee and elbow, the systems and methods described herein may be used to treat other joints such as ankles, wrists, shoulder and spine.

As will be seen in the following description, the systems and methods described herein relate to the concomitant application of temperature regulated compression along with rigid support to certain injured portions of the human body. In particular, these systems and methods relate to a brace to be fitted around a joint of a human for applying therapeutic temperature regulated compression to the joint and having hinged supports disposed therein to provide support sufficient to allow the patient to conduct intensive daily activities such as walking, jumping, writing, throwing and lifting.

Figure 1:
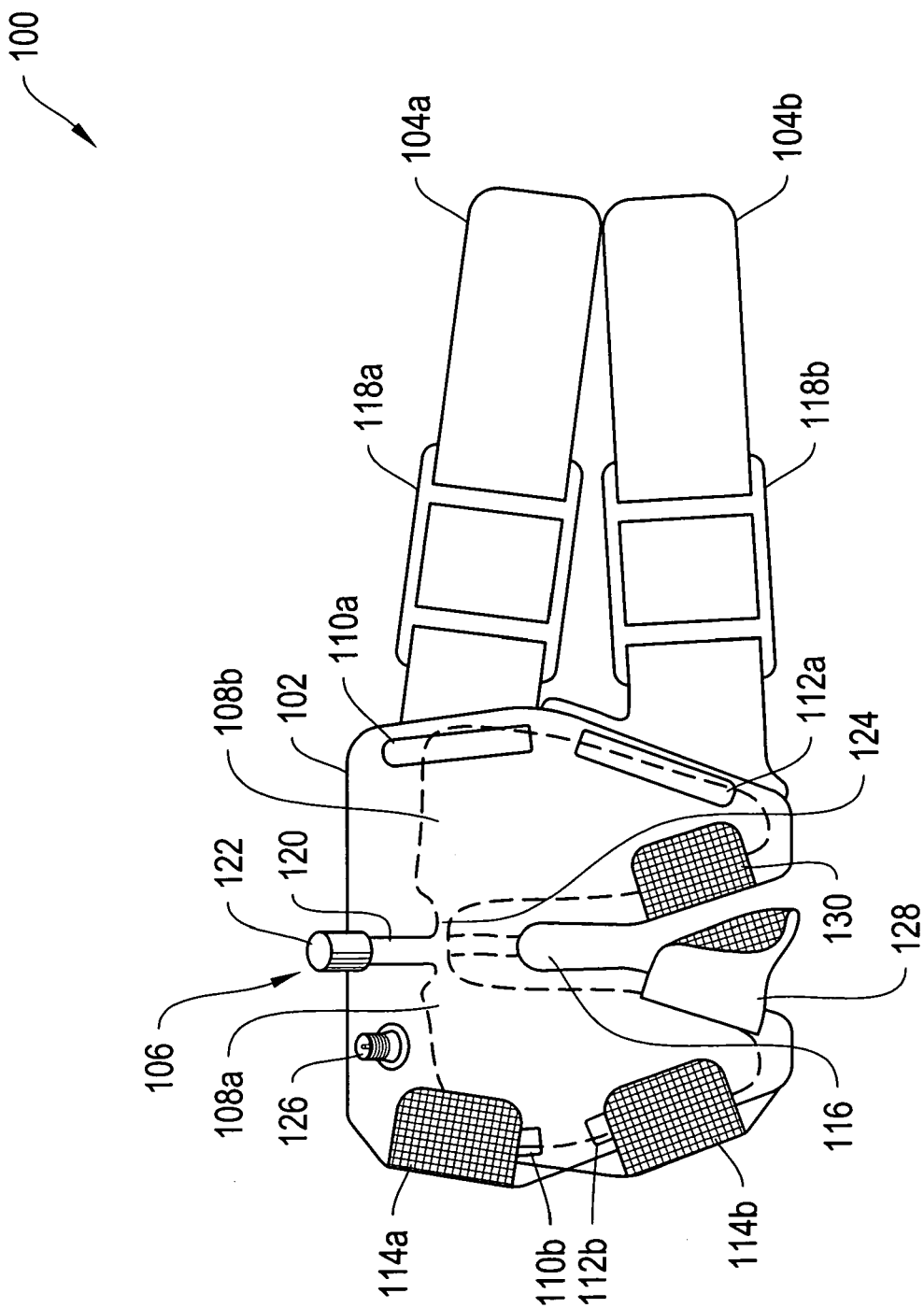
FIG. 1 depicts one view of a temperature regulated compression brace, according to an illustrative embodiment of the invention.

FIG. 1 depicts a view of a temperature regulated compression brace 100 according to an illustrative embodiment of the invention. The brace 100 is designed to be applied to the knee of the leg of an individual. The brace 100 includes a shell 102, a proximal strap 104a and a distal strap 104b (collectively, the "strap 104") that can hold the shell 102 in place. The depicted embodiment has a fluid port 106 in fluid communication with two fluid compartments 108a and 108b (collectively, the "fluid compartment 108"). The fluid port 106 includes a neck portion 120 and a closable opening 122 for admitting fluid into the interior of the brace 100. The illustrated fluid compartment 108 is internally disposed within the shell 102, as shown by dotted lines. FIG. 1 further depicts an embodiment that has four pockets, 110a, 112a, 110b and 112b, one proximal and one distal, disposed on the shell 102 on each side of the brace 100 (collectively, the "pockets 110 and 112"). The pockets 110 and 112 are configured to accommodate bracing and/or reinforcing structures such as rigid members including plates and rods. The bracing structures may help provide necessary support for the knee of an individual. The reinforcing structures may help maintain the structural integrity of the brace 100 during use. The pockets 110b and 112b are partially obscured by Velcro® strips 114a and 114b. Consequently, the pockets 110b and 112b are shown again in FIG. 2, with the Velcro® strips 114a and 114b (collectively, the "strips 114") differently oriented and without the dotted lines depicting the interior fluid compartment 108.

Figure 3:
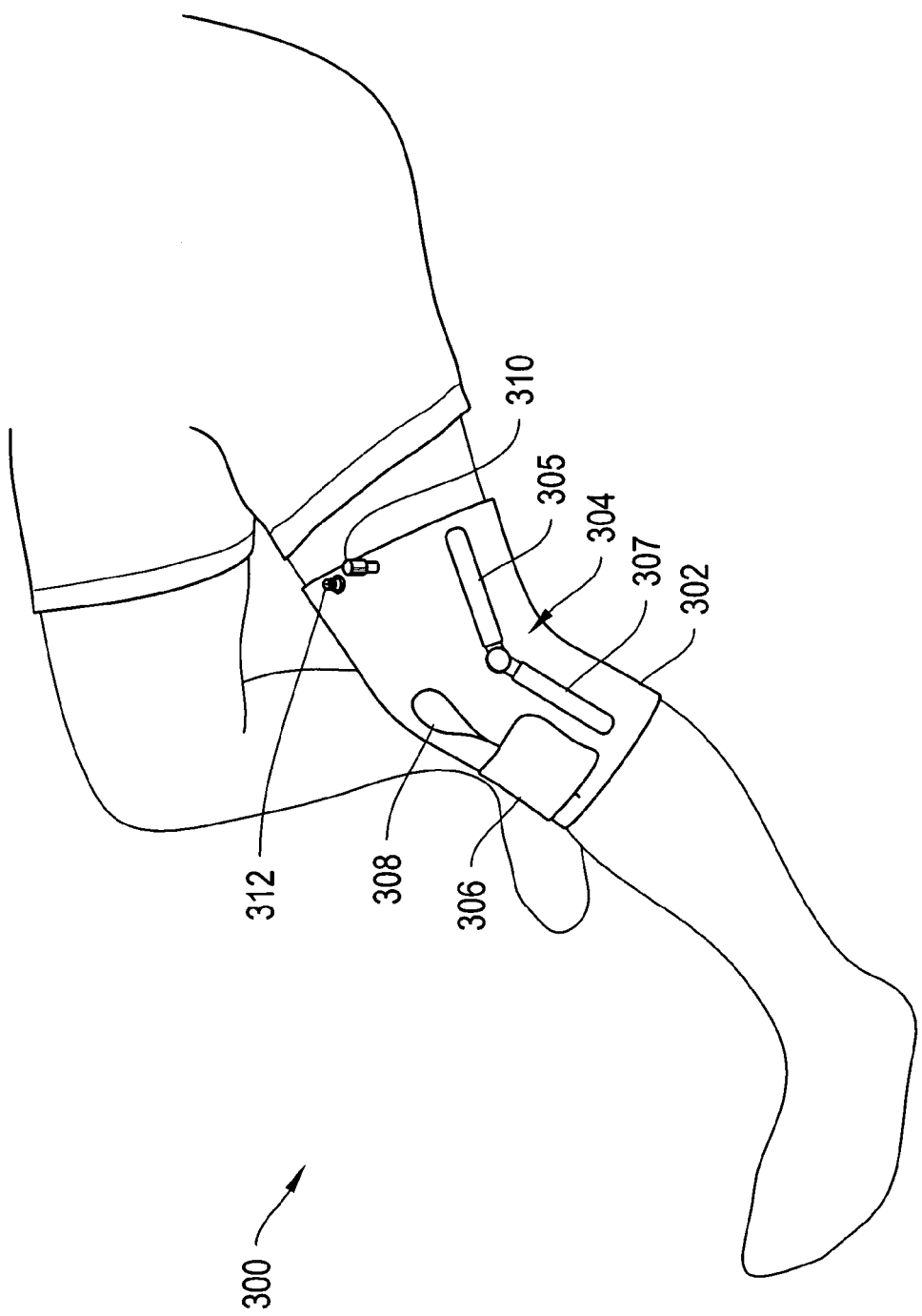
FIG. 3 depicts the temperature regulated compression brace as applied to a patient's knee, according to an illustrative embodiment of the invention.

The depicted brace 100 is configured so it can be wrapped about a patient's knee. To apply the brace 100, as seen in FIG. 3, the notch 116 is placed near the Patella area and the shell 102 is wrapped behind the knee by the proximal strap 104a and the distal strap 104b, so as to be secured to the strips 114 on the lateral side of the knee. The notch 116 in the brace 100 is intended to receive the knee cap or patella so as to shield the patella or kneecap of the patient from the pressure and temperature effects of the brace 100. The proximal strap 104a and a distal strap 104b are attached to brace 100.

In one embodiment strap 104 is made of any well-known flexible material having a portion with a fastening material thereon known as VELCRO®. Straps 104 are made of a relatively inelastic material. Straps 104a and 104b are arranged for attaching relationship with mating Velcro® strips 114a and 114b. The Straps 104a and 104b may have optional resilient foam attachments 118a and 118b attached respectively thereto for the purpose of providing a cushion for the underside of the person's leg to which the temperature regulated compression brace 100 is attached.

Fastening strips 128 and 130 are also included and are configured to close a portion of the notch 116 below the kneecap when connected. The fastening material for the fastening strips 128, 130, 114a and 114b includes any type of fastening without departing from the scope of the invention.

As shown by dotted lines in FIG. 1, the brace 100 includes at least one, and typically two or more, fluid compartments 108, respectively. Each fluid compartment 108 is adapted for receiving and containing the fluid regulated at a desired temperature and pressure or within a desired range and for making generally uniform and abutting contact with the encompassed portion of the leg being treated. In certain embodiments, the fluid compartment 108 includes a fluid at a desired temperature. In certain embodiments the fluid compartment 108 is flexible, such that it can expand when fluid is placed therein and thereby apply compression against the patient's limb. In other embodiments the fluid compartment 108 is inflexible and is held in compressive contact with the limb by one or more straps, or other approaches.

As shown, an internal siphon 124 connects the neck portion 120 and closable opening 122 of the fluid port for filling and draining the temperature regulated fluid from the fluid compartments. Draining is typically important for re-chilling the fluid warmed during extended therapy. To aid in filling the fluid compartment 108, the brace 100 may include an air release valve 126 that allows air to escape from the fluid compartment 108 as liquid is poured into these compartments via fluid port 106. Opening the air release valve 126 may also be useful when draining the fluid compartments 108.

The brace 100 may also include an optional layer of insulation to assist in regulating the temperature of the brace 100. In certain embodiments, open cell urethane foam is used. For example, an open-cell urethane foam material is used having a thickness of approximately 0.30" thick and will compress to about half its normal thickness under a 1 psi load. The optional layer of insulation assists in maintaining the temperature of the fluid for an extended period of time.

FIG. 2A depicts a temperature regulated compression brace 200, similar to brace 100 in FIG. 1, according to another illustrative embodiment of the invention. The brace 200 includes (not shown) fluid compartments 108 similar to brace 100. The brace 200 includes internal siphons 210a and 210b (collectively, the "internal siphon 210") in fluid connection with the fluid port 106 and the corresponding fluid compartments 108a and 108b. The brace 200 also includes support systems 202a and 202b (collectively, the "support system 202") that extend along the sides of the brace 200 such that when the brace 200 is wrapped around the patient's knee, one support system 202 will be located along the internal side of the knee and the other support system 202 will extend along the external side. Both support systems 202 will be outward facing on the exterior surface of the brace 200 and disposed away from the patient's knee. The support system 202a includes a proximal rigid member 204a, a distal rigid member 206a (collectively, the "rigid members 204 and 206), and a hinge 208a disposed therebetween and adapted to adjustably confine the rigid members 204a and 206a at a pre-determined angle 207. Support system 202b similarly includes a proximal rigid member 204b, distal rigid member 206b (collectively, the "rigid members 204 and 206), and a hinge 208b and adapted to adjustably confine the rigid members 204a and 206a at a pre-determined angle 209.

In the depicted embodiment, each of rigid members 204 and 206 is a metallic member typically formed of steel and having a thickness suitable to provide support to the patient's knee. In other embodiments, the rigid members 204 and 206 may be formed from rigid polymeric materials including polycarbonates and plastics. The rigid members 204 and 206 extend along a portion of the height of the brace 200. The proximal rigid members 204 extend along the proximal portion of the brace 200 and are configured to be positioned alongside the thigh portion of the leg above the knee. The distal rigid members 206 extend along the distal portion of the brace 200 and are configured to be positioned alongside the upper calf portion of the leg below the knee. The rigid members 204 and 206, alone or in combination, provide structural support to the joint as well as to the brace 200. During operation, the brace 200 may undergo an alteration in shape due to the expansion of one or more fluid compartments 108. The rigid members 204 and 206 assist in maintaining the structural integrity of the brace 200 during expansion and/or contraction. The rigid members 204 and 206 may also serve as a splinter to restrict the movement of the limb and thereby facilitate quicker recovery from injuries. In one embodiment, the proximal rigid members 204 and 206 and the distal rigid members 206 may be connected through hinges 208a and 208b. The hinges 208a and 208b allow pivoting motion of the rigid members 204 and 206.

In the depicted embodiment, the hinges 208a and 208b, respectively (collectively, the "hinge 208"), includes a lockable hinge. The lockable hinge 208 allows the user to select the degree at which the knee will be bent. For the lockable embodiment, each hinge 208 may comprise a screw fitting that will lock the hinge, by a rotating action, into the selected orientation. Optionally, each hinge may be key-operated, such that a key is engaged into the depicted slot and rotated so that the hinge is locked into place. In certain embodiments, the hinge 208 has a ratchet mechanism that limits the angular orientation of the hinge to a select few positions. In certain embodiments one or more of the hinges are configured to rotate and lock only in selected orientations. For example, selected orientations may include multiples of 10° or of 15°. As depicted in FIG. 2A, the hinge 208a may be adjusted so as to establish an angle 207 between the rigid members 206a and 204a. In certain embodiments the angle 207 is less than 180° but it can be adjusted to reduce that angle as desired. Any number of different types of hinges 208 and rigid members 204 and 206 may be used without departing from the scope of the invention, such as those disclosed in U.S. patent application Ser. No. 10/357,990 for a "Multi-functional Joint Brace", which is herein incorporated by reference in its entirety.

Any suitable support member may be used, including solid unhinged members, as well as hinged supports that have any suitable hinge or optional locking mechanism. Typically, the support is formed of metal, such as steel, but in other embodiments it may be plastic, fiberglass or some other suitable material. In further optional embodiments, there may be only one support member 202 used in the brace 200, with that support member being sufficiently strong to provide the appropriate bracing. Similarly, there may be more than two supports, if additional supports would aid a particular patient. In the embodiment depicted, the supports 202 are located on either side of the knee and extend along the mid section of the brace 200. In other embodiments, the rigid supports 202 may be longer, extending along the full length of the brace 200 from top to bottom. Optional strapping may be provided as well, to allow the supports to strap more directly to the patient's limb and thereby provide a more secure grip, and reduce the tendency for the brace 200 to droop.

In the depicted embodiment, the proximal rigid members 204 are fitted into proximal pockets 110 and the distal rigid members 206 are fitted into distal pockets 112. In one embodiment, the rigid members 204 and 206 are removable from the pockets 110 and 112 and thus the brace 200 may be used with or without the support system 202. In certain embodiments, the brace 200 is used simply with at least one fluid compartment 108 and one or more rigid members 204 and 206.

Various parts of the support system 202 may be joined together. Exemplary suitable joining mechanisms include hook and loop fasteners, adhesive, stitching, or any other suitable means.

FIG. 2B depicts a cross-sectional side view of the temperature regulated compression brace 200 of FIG. 2A according to another illustrative embodiment of the invention. In particular, FIG. 2B shows coextensive fluid compartments 212a and 213a, and 212b and 213b (collectively, the "compartments 212 and 213"). Outer compartment 212a has an outer wall 214a and inner compartment 213a has an outer wall 216a. Similarly, outer compartment 212b has an outer wall 214b and inner compartment 213b has an outer wall 216b. The inner compartments 213a and 213b (collectively, the "inner compartment 213") are adapted for receiving and containing the temperature regulated fluid in generally uniform and abutting contact via wall 220 of the shell 102 with the encompassed portion of the joint being treated. A pair of internal siphon tubes 210a and 210b (collectively, the "internal siphon 210") connects the neck portion 120 of the fluid port 106 with the inner compartment 213. Fluid travels into the fluid compartment through openings 218a and 218b (collectively, a "siphon opening 218") in the internal siphon 210. The outer compartments 212a and 212b (collectively, the "outer compartment 212") contain foam, fiberglass, or other padding or material for insulating the underlying inner fluid compartment 213 and for preventing sweating of the outer surface of the shell 102. The outer compartment 212 helps maintain the shape of the brace 200 while permitting the expansion of the inner fluid compartment 213 when filled with fluid. In certain embodiments, the outer walls 214, 216 and 220 may be formed from waterproof materials, breathable materials, or other desired materials.

In operation, as thermal fluid fills the inner compartment 213, it expands the brace 200, compresses the limb and tightens the straps 104. The brace 200 would expand about the limb and both straps would be tensioned around the upper and lower limb. In certain situations, for example, where swelling occurs, after knee surgery of a suprapatellar pouch (immediately above the knee), it is medically desirable to apply more compression in the proximal area above the patella and less in the distal area. Additionally, the risk of undesirable constriction is greater under the distal strap below the knee.

FIG. 3 depicts the temperature regulated compression brace 300 as applied to a Patient's knee, according to an illustrative embodiment of the invention. The regulated compression brace 300 is similar to braces 100 and 200 shown in FIGS. 1, 2A and 2B. Brace 300 includes a shell 302 having a support system 304, a fluid port 310 and an air release valve 312. The support system 304 includes rigid members and a hinge. The brace 300 further includes an expandable fluid compartment (not shown) in direct or indirect fluid communication with the fluid port 310. The brace has a notch 308 to accommodate the knee and one or more straps 306 and attachment assembly (e.g. VELCRO™) for removably securing the shell 302 to the knee.

In one embodiment, the brace is initially in a fanned-out position having a view similar to the views shown in FIGS. 1 and 2A. The brace 300 is placed on the knee of an individual such that the notch 308 is aligned with the patella or kneecap. The shell 302 is wrapped around the leg to surround the knee, such that the support system 304 is stationed on the interior (medial) and exterior (lateral) sides of the knee cap. The one or more straps 306 is attached to an attachment assembly, such as a VELCRO™ strap, and tightened to secure the brace 300 to the leg. Attaching the strap 306 closes a portion of the notch 308 that was initially located below the kneecap. Temperature regulated fluid is introduced into the fluid compartments through the fluid port 310. The temperature regulated fluid fills the fluid compartment and thereby causes it to expand. The expanding fluid compartment compresses the joint and surrounding region to stabilize the joint, while concomitantly, the temperature regulated fluid provides heating or cooling therapy. In certain embodiments, the fluid is regulated to maintain a temperature below room temperature and close to freezing temperatures to provide cold therapy to the location of the joint. The fluid can also be regulated to maintain a temperature above room temperature and to provide heat therapy to the location of the joint.

As noted earlier, the support system 304 includes rigid members and a hinge, which may be adapted to stabilize the limb as the fluid compartment compresses the limb and the fluid temperature provides heating or cooling therapy. The hinge may be lockable to prevent hyper-extension of the joint. Prior to the application of the brace 300 on the knee, the hinge may be in an unlocked state such that the rigid members can pivot freely about the hinge. Once the brace 300 is secured to the knee, the hinge may be selectably locked to allow the rigid members to pivot about the hinge, however restricted to a certain desired range previously selected.

Figures 4A, 4B:
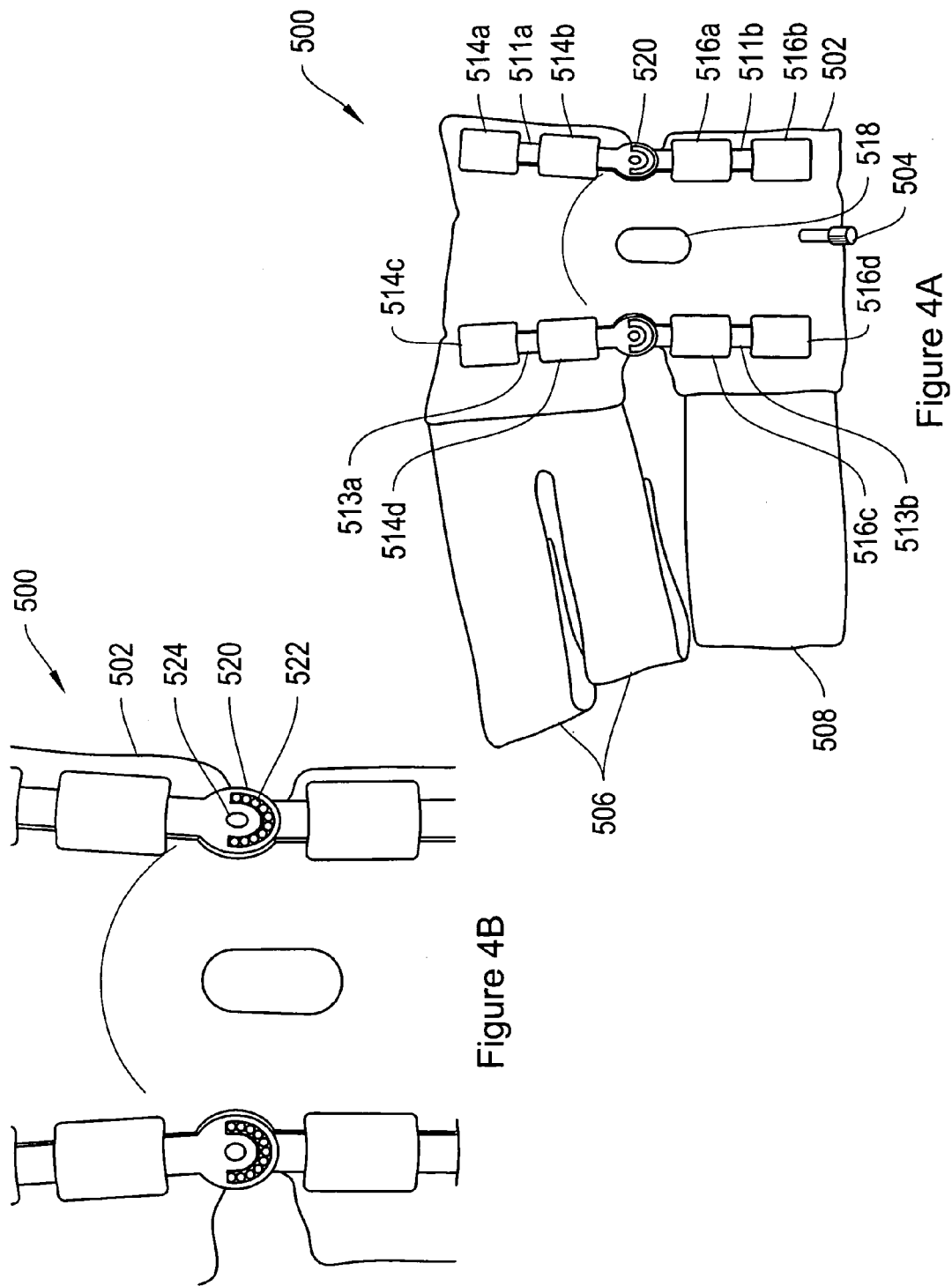
FIGS. 4A and 4B depict an embodiment of a brace, according to an illustrative embodiment of the invention.

FIGS. 4A and 4B depict one embodiment of the brace 500 as designed to be applied to the knee of the leg of an individual. As described above, the brace 500 includes a shell 502 and two proximal straps 506 and a distal strap 508 that can hold the brace 500 in place. There is a fluid port 504 that is in fluid communication with the fluid compartments formed within the shell 502. The brace 500 may be applied to the patient's knee and attached to a fluid reservoir (a reservoir bottle) by way of a valve. The valve may be of the type that can be disconnected from the reservoir bottle and will include a valve or stop that will allow the user to walk about with the wrap on and with the fluid contained in the wrap. In the illustrated embodiment, the brace 500 includes two support systems each having two rigid members that are coupled in a hinge assembly 520. One set of rigid members removably or permanently fits into pockets 514a, 514b, 516a and 516b. Another set of rigid members removably or permanently fits into pockets 514c, 514d, 516c and 516d (collectively, the "pockets 514 and 516"). In one embodiment, the pockets 514 and 516 include a strap attachment layer such as VELCRO™. In such an embodiment, when the brace 500 is wrapped around the knee, the straps 506 fold around the back of the knee and attach to the strap attachment layer on the top of pockets 514. Similarly, strap 508 folds around the back of the knee and attaches to the strap attachment layer on the top of pockets 516. The brace 500 includes an aperture 518 for accommodating the patella or kneecap. The aperture 518 has a function similar to that of the notch 116 of brace 100 in FIG. 1 and notch 308 of brace 300 in FIG. 3. The shell 502 is tapered near the location of the hinge 520 and in between the straps 506 and strap 508. The tapered shape of the shell 502 allows the brace 500 to conform to the normal flexing of the leg about the knee.

FIG. 4B depicts a close-up view of the brace 500 according to one illustrative embodiment of the invention. In particular, the selectably lockable hinge 520 is more clearly depicted. The hinge 520 comprises a range of different angular levels 522 and a central pivot point 524. The angular levels 522 allows a user to restrict the pivoting action of the rigid members about the pivot point 524 to one or more of a select number of angular levels 522. The hinge 520 may be adapted to be set at one or more different angular levels and may be lockable and/or selectable.

Figure 5:
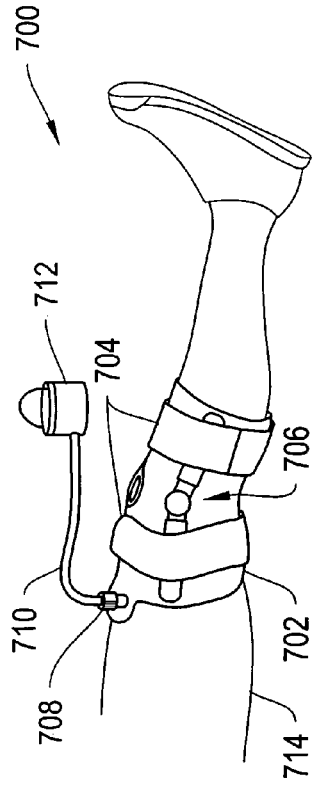
FIG. 5 depicts an embodiment of a temperature regulated compression system having a brace designed to be applied to a person's knee, according to an illustrative embodiment of the invention.

In certain embodiments, the straps secure the brace to the joint in a snug but not tight manner. The tightness of the fit can be affected by circulating pressurized fluid into the brace. The brace may be combined with external components capable of supplying temperature controlled pressurized fluid to the brace. FIG. 5 depicts one prototype embodiment of a temperature regulated compression system 700 having a brace designed to be applied to the knee of the leg 714 of an individual. The brace may be pressurized with a fluid from an elevated fluid reservoir 712. In particular, the brace in system 700 is similar to braces 100, 200, 300 and 500. The brace includes a shell 702, straps 704, support system 706, fluid port 708 and internal fluid compartments. The fluid port 708 is connected to the fluid reservoir 712 by tubing 710. During operation, fluid from the fluid reservoir 712 may flow through the tubing and fluid port 708 into the brace.

The fluid reservoir 712 may be a flexible pouch or a rigid container and is configured to hold a fluid such as ice and water. In certain embodiments, the fluid reservoir 712 is configured to hold a fluid sufficient for six to eight hours of cryotherapy. The reservoir 712 includes a lid and handle and is coupled with tubing 710 to the fluid port 708 on the brace in system 700.

In one embodiment, during operation, the brace of system 700 is applied to the limb and the fluid reservoir 712 containing cold water is elevated above the limb and the ice chilled water flows into the fluid compartments within the brace. Compression of the limb, due to the gravity flow of the ice water, is proportional to the elevation of the fluid reservoir 712 with respect to the brace. A manually operated valve may be connected along the length of the tubing 710 to control the flow of ice water and allow the flow to be stopped when a desired pressure is reached by manually closing the valve. Thus, the pressure is sealed in the brace and the skin temperature falls rapidly. In one embodiment, after 15 to 30 minutes, body heat will warm the water in the brace. The water is then "re-chilled" by reversing the cycle. The fluid reservoir 712 is lowered below the leg and the manual valve is opened. The warmed water is drained back into the reservoir 712. After a short interval allowing mixing of the water with the ice, the fluid reservoir 712 is again elevated and the brace-filling process repeated. Thus, a closed chilled water system is used and the water is re-circulated between the fluid reservoir 712 and the brace in the closed system to maintain the water at the desired temperature. As pointed out previously, it will be noted in FIGS. 1 and 2A that the internal siphon tubes 210a and 210b extend to the distal areas of the fluid compartments 108a and 108b, thus either draining the warm water from or filling the compartment with cold water as set forth above. When filling the fluid compartment 108 with cold water, the air release valve 126 (FIGS. 1, 2A and 2B) may be opened to allow air to escape as the chilled water is entering the fluid compartments 108.

Figure 7:
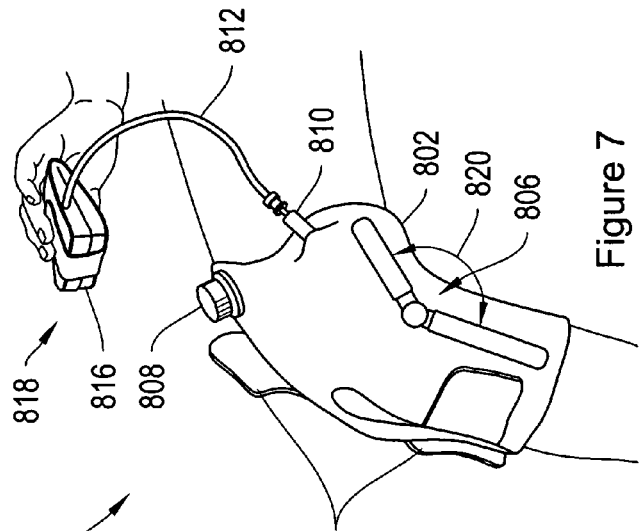
FIGS. 6 and 7 depict a brace connected to a fluid source, according to an illustrative embodiment of the invention.
Figure 6:
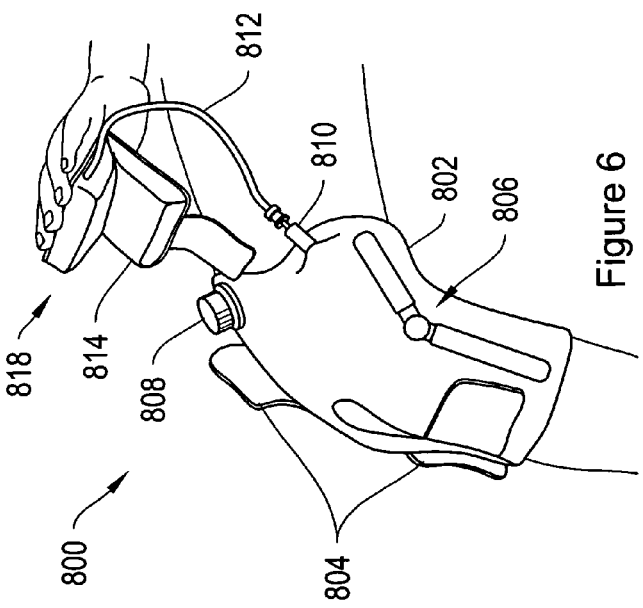

During operation, the circulation of fluid in the fluid compartment 108 causes the expansion and contraction of the fluid compartment. The rigid support system 706 helps maintain the structural integrity of the brace of system 700 during the expansion and contraction of the fluid compartments. The support system 706 may also allow a patient to simultaneously avail of bracing features in combination with temperature regulated compression. FIGS. 6 and 7 depict additional features that may be combined with bracing.

As seen in FIG. 2B, the brace 200 includes an inner fluid compartment 213 and an outer compartment 212. In certain embodiments, pressure sources external to the brace 200 are used to cause the outer walls 216 of the fluid compartment 213 to more uniformly engage the body area being treated. In such embodiments, pressurized fluid is introduced into the outer compartment 212. FIGS. 6 and 7 depict a brace 800 connected to a pump 818, according one illustrative embodiment of the invention. In particular, the brace 800 is shown secured to a joint and includes a shell 802, straps 804 in an attached position, support system 806 and a fluid port 808. The fluid port 808 is in fluid communication with the inner fluid compartment 213 (depicted in FIG. 2B). The fluid port 808 is shown larger than fluid port 708 of FIG. 5. The brace 800 also includes a second fluid port 810 in fluid communication with the outer compartment 212. The second fluid port is connected to a pump 818 via tubing 812. The pump 818 is shown in an open position 814 in FIG. 6 and in a closed position 816 in FIG. 7.

During operation, the pump 818 is shown to be hand squeezed to go from an open state 814 in FIG. 6 to a folded state 816 shown in FIG. 7. Squeezing the pump 818 causes pressurized fluid such as air to pass through the tubing 812 and second fluid port 810 into the brace 800. The pressurized fluid (air) enters the outer compartment 212 and applies pressure against the outer wall 216 of the inner fluid compartment 213. The applied pressure on the outer wall 216 of the inner compartment 213 causes the inner fluid compartment 213 with its thermal fluid to be in pressure engagement with the encompassed portion of the leg.

In one embodiment, the pump 818 includes a rectangular body portion to which is attached a strap having a VEL-CRO™ strip thereon. The pump 818 may be folded about its center and the VELCRO™ strap wrapped around the open end of the pump to have a mating contact with a second VELCRO™ strip on the obverse side of the pump. The pump 818 may be formed from air impervious resilient material such as plastic. The pump may include layers of rigid material and/or layers of foam material. Other types of pumps may be used for supplying pressurized fluids without departing from the scope of the invention.

Figure 8:
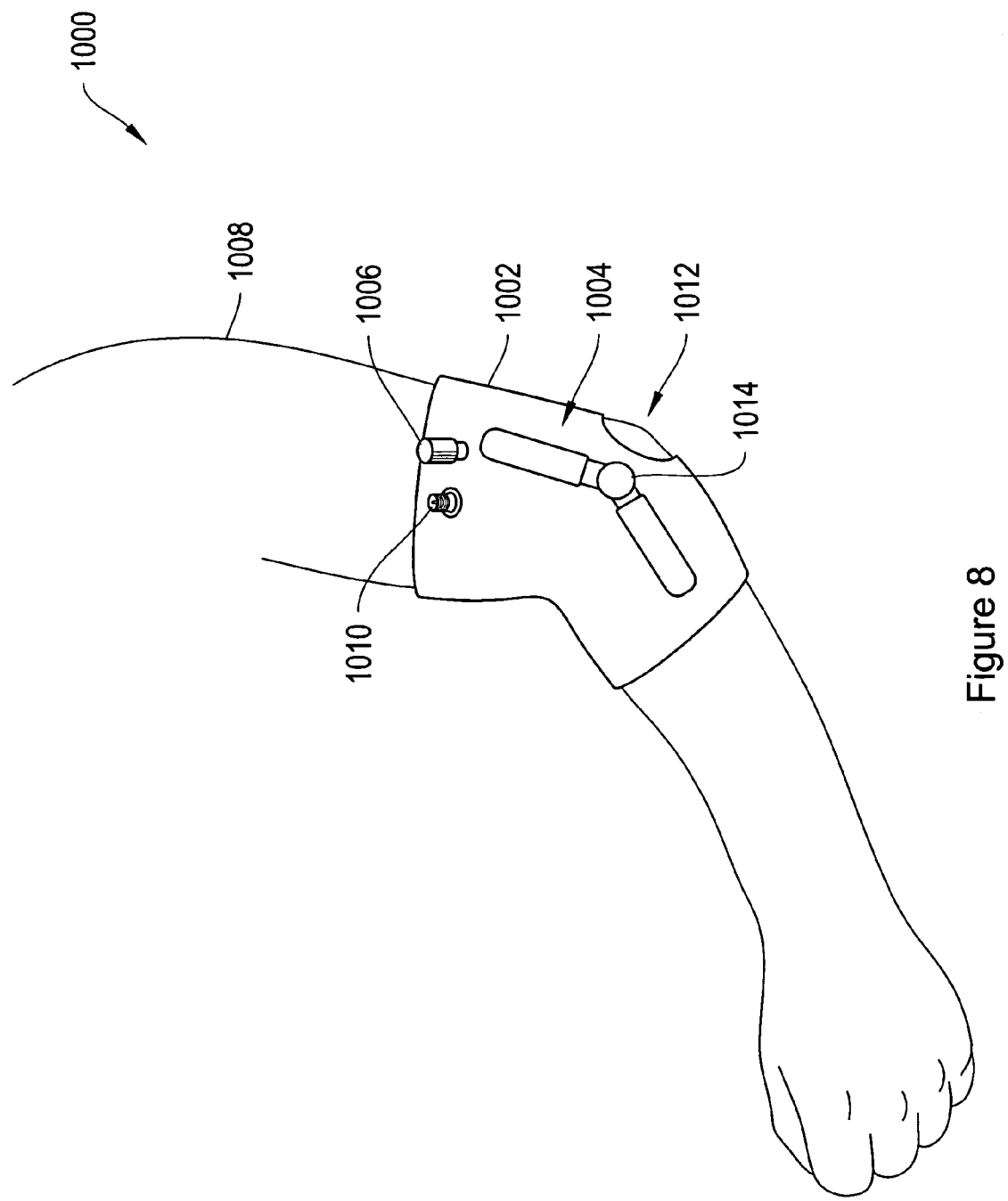
FIG. 8 depicts a temperature regulated compression brace as applied to a Patient's elbow, according to an illustrative embodiment of the invention.

FIG. 8 depicts a temperature regulated compression brace 1000 as applied to a Patient's elbow, according to an illustrative embodiment of the invention. The brace 1000 is similar to braces 100, 200 and 300 shown in FIGS. 1, 2A, 2B, and 3. Brace 1000 includes a shell 1002 having disposed thereon a support system 1004, a fluid port 1006 and an air release valve 1010. The support system 1004 includes rigid members and a hinge. The brace 1000 further includes an expandable fluid compartment in direct or indirect fluid communication with the fluid port 1006. The brace has a notch 1012 to accommodate the elbow joint.

In one embodiment, the brace 1000 is slid over the arm 1008 of an individual such that the notch is aligned with the elbow joint and the brace is snugly fit. An alternate embodiment for the elbow could be similar to brace 500 in FIG. 4A configured as a wrap instead of a sleeve with aperture 518 accommodating the elbow. The brace 1000 is oriented such that the support system 1004 is stationed on the interior (medial) and exterior (lateral) sides of the elbow joint. Temperature regulated fluid is introduced into the fluid compartments through the fluid port 1006. The temperature regulated fluid fills the fluid compartment and thereby causes it to expand. The expanding fluid compartment compresses the region of joint to stabilize the joint, while the temperature regulated fluid provides thermal therapy. For example, the fluid can be regulated to maintain a temperature below room temperature and close to freezing temperatures to provide cold therapy to the location of the joint. The fluid can also be regulated to maintain a temperature above room temperature and to provide heat therapy to the location of the joint.

As noted earlier, the support system 1004 includes rigid members and a hinge 1014. The hinge 1014 may be lockable to prevent hyper-extension of the elbow. Prior to the application of the brace 1000 on the elbow, the hinge 1014 may be in an unlocked state such that the rigid members can pivot freely about the hinge 1014. Once the brace 1000 is secured to the elbow, the hinge 1014 may be locked to allow the rigid members to pivot about the hinge 1014 within a certain desired range.

In certain embodiments, the support system 1004 of brace 1000 is configured to restrict movement of the elbow along the elbow joint. In such embodiments, the support system 1004 is configured along at least one of the humerus, radius and ulna bones. The support system 1004 may be configured to restrict movement along any hinged-joint in the patient.

Figure 9:
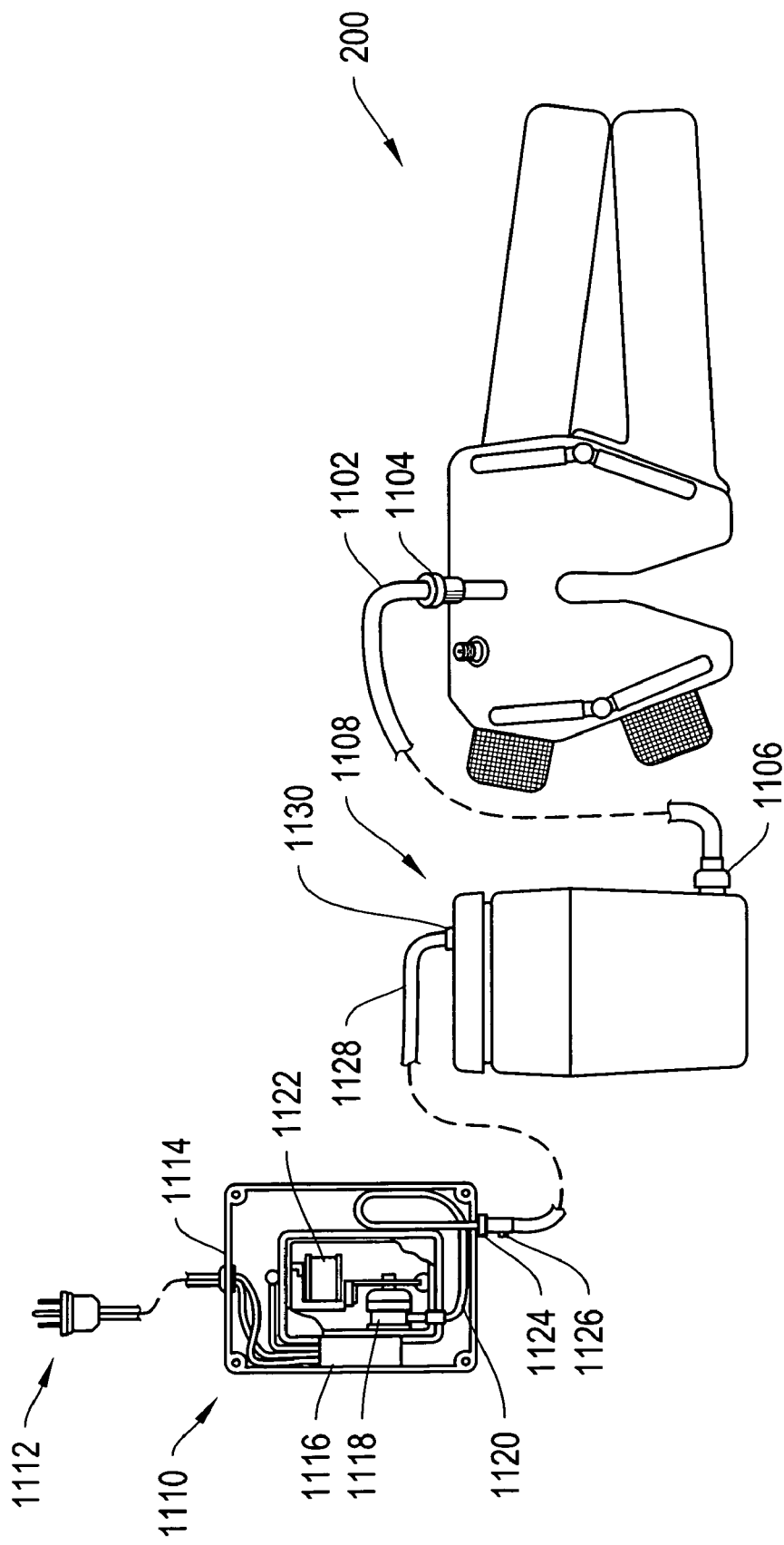
FIG. 9 depicts a brace connected to a fluid source, according to an illustrative embodiment of the invention.

FIG. 9 is a diagrammatic representation of an alternative embodiment of the present invention. In FIG. 9, a fluid reservoir 1108 is coupled to brace 200 with tubing 1102 and connectors 1104 and 1106. FIG. 9 includes pump unit 1110 having an air pump 1118, an electrical timer 1116, and a motor 1122 in a common housing 1114 that can be plugged into a wall socket by means of a plug-in-type terminal 1112. During operation, the air pump 1118 applies pressure and forces fluid from the fluid reservoir 1108 into the brace 200. Air pump 1118 is a standard vibratory air pump such as that used in aquariums and may be manufactured by Eiko Electric in Taiwan. Timer 1116 is a timer of a type well known in the art such as those manufactured by Control Products Corp. in Grafton, Wis. Timer 1116 is preferably solid-state and may be arranged to have a desired duty cycle. An exemplary duty cycle useful in the instant invention is 30 seconds ON and 30 seconds OFF. Thus, motor 1122 is turned ON for 30 seconds and pump unit 1110 pumps air through hose 1120 within pump unit 1110 to connector 1124 having bleed valve 1126 and through external air hose 1128 to connector 1130 of fluid reservoir 1108. As motor 1122 runs for 30 seconds, it causes pump 1118 to pressurize fluid reservoir 1108, thus forcing a predetermined volume of chilled fluid through connector 1106, tubing 1102, and connector 1104 to the interior of brace 200. A fluid flow control valve near connector 1104 may be used to control the amount of fluid flowing from the tubing 1102 into the brace 200 to prevent overcooling by restricting fluid flow into brace 200.

The increased flow of water into the brace 200 also increases compression on the limb in contact with brace 200 during the ON cycle, and the compression falls as the water returns to reservoir 1108 during the OFF cycle. When the top of fluid reservoir 1108 is about the same elevation as brace 200, the pressure oscillates between about 5-to-15 mmHg above atmospheric pressure. When the top of reservoir 1108 is about 8 inches above brace 200, the pressure oscillates between about 15 to about 35 mmHg above atmospheric pressure. Thus, the system provides a continuous application of cold fluid for applying cold therapy to the limb, as well as oscillating compression of a predictable and adjustable magnitude.

Because the water flows back and forth between reservoir 1108 and brace 200, only a single connecting tubing 1102 is required with single connectors 1106 and 1104 to reservoir 1108 and brace 200, respectively. Within brace 200, the efficient exchange of cold water for warm may be enhanced by one-way check valves installed between the neck portion of the fluid port and an internal siphon. The check valve opens during the ON cycle to permit pressurized water to flow from reservoir 1108 into the top of brace 200, but closes during the OFF cycle and forces return of warmer water to reservoir 1108 through the ends of the internal siphon, which extend substantially to the bottom of brace 200. The oscillating pressurization of fluid reservoir 1108 on a cyclical basis provides the necessary compression and decompression of brace 200. A typical system for thermal compression is disclosed in U.S. Pat. No. 5,314,455 to Johnson Jr. et al. for a "Thermal Compress System," which is herein incorporated by reference in its entirety.

In certain alternative embodiments, an exemplary brace includes one or more heating elements disposed within the shell. The heating elements such as electrical resistive heating elements may be positioned near the fluid compartments. Such heating elements, when connected to an electrical power source, generate the necessary heat to increase the temperature of the fluid in the fluid compartment. Therefore, the heating elements may help maintain the thermal energy of the temperature regulated fluid at a desired level. In certain embodiments, the heating and/or cooling elements include chemicals disposed in the brace that are capable of producing exothermic and/or endothermic reactions with air and the material of the brace. Such chemicals may be disposed near the fluid compartment or as a filling in the outer compartment. The shell of the brace may also include an opening to place such chemicals within the vicinity of the joint.

In other embodiments, the brace may include electrical control circuitry. The electrical control circuitry may include printed circuit cards having circuits and devices for operating and controlling valves, temperature regulators, internal and external pumps and other motors, relays and timers. The electrical circuitry may be linked with an external computer terminal for saving patient data. The electrical circuitry may help patients during the recovery period after an injury when certain types of exercises are required. For example, the electrical circuitry may be connected to the support system, and through a motor to a computer terminal. Software in the computer terminal can control the operation and locking conditions of the hinges and rigid members of the support system as desired. The software system may also control the operation of fluid flow to and from the fluid compartments using timers and pumps. In certain embodiments, the fluid flow may be operated in discrete time intervals and the support system including hinge/rigid member assembly may be electronically synchronized with the fluid flow to allow temperature regulated compression along with physiotherapy.

In certain embodiments, a support system, such as those in the braces shown in FIGS. 1-9 may have rigid members and hinges positioned along selected portions of the limb. In such embodiments, the rigid members are positioned along at least one of lateral, medial, posterior and anterior sides of the limb. FIGS. 10A and 10B depict a perspective view and a side view, respectively, of a brace 1300 having support systems 1304 disposed on the anterior and posterior sides of a knee joint, according to an illustrative embodiment. The support system 1304 on the anterior side (FIG. 10A) includes rigid members 1305 and 1307, each having a cylindrical end portion. A more detailed view of the support system 1304 is depicted in FIG. 10C. The rigid members 1305 and 1307 are attached to each other and slide into pockets 1314a and 1314b, respectively (FIG. 10B). Similarly, posterior rigid members 1305 and 1307 slide into pockets 1314c and 1314d, respectively. The pockets 1314a, 1314b, 1314c and 1314d (collectively, the "pockets 1314") are shown to be attached to the flexible shell 1302 of brace 1300. In certain embodiments, the pockets 1314 are unitarily formed with the flexible shell 1302. The brace 1300 also includes a fluid port 1310 in fluid communication with a fluid compartment (not shown) disposed within the flexible shell 1302. The brace 1300 additionally includes an air release valve 1312 similar to air release valve 312 of FIG. 3. The brace 1300 further includes a notch or aperture 1308 to accommodate the patella or knee cap and one or more straps 1306 and attachment assembly (e.g. VELCRO™ for removably securing the shell 1302 to the knee.

In certain embodiments, the brace is initially in a fanned-out position having a view similar to the views shown in FIGS. 1 and 2A. The brace 1300 is placed on the knee of an individual such that the notch 1308 is aligned with the patella or kneecap. The shell 1302 is wrapped around the leg to surround the knee, such that the support system 1304 is stationed on the anterior and posterior sides of the knee cap. The one or more straps 1306 is attached to an attachment assembly, such as a VELCRO™ strap, and tightened to secure the brace 1300 to the leg. Attaching the strap 1306 closes a portion of the notch 1308 that was initially located below the kneecap. Temperature regulated fluid is introduced into the fluid compartments through the fluid port 1310. The temperature regulated fluid fills the fluid compartment and thereby causes it to expand. The expanding fluid compartment compresses the region of joint to stabilize the joint, while providing thermal therapy. In certain embodiments, the fluid is regulated to maintain a temperature below room temperature and close to freezing temperatures to provide cold therapy to the location of the joint. The fluid can also be regulated to maintain a temperature above room temperature and to provide heat therapy to the location of the joint.

As noted earlier, the support system 1304 includes rigid members 1305 and 1307 and a hinge 1309. The hinge 1309 may be lockable to prevent hyper-extension of the joint. Prior to the application of the brace 1300 on the knee, the hinge 1309 may be in an unlocked state such that the rigid members can pivot freely about the hinge 1309. Once the brace 1300 is secured to the knee, the hinge may be selectably locked to allow the rigid members to pivot about the hinge, within a certain desired range, as described above.

FIG. 10C depicts a three-dimensional view of the support system 1304 according to an illustrative embodiment. The support system 1304 includes rigid members 1305 and 1307, each having a cylindrical end portion. The cylindrical end portion includes one or more cylindrical teeth. The cylindrical teeth are sized, shaped and positioned such that the cylindrical teeth of rigid member 1305 interlocks with the cylindrical teeth of rigid member 1307 to form the support system 1304. The interlocked rigid members 1305 and 1307 are coupled to each other through a pin 1318. The interlocked support system assembly has the appearance of a single rigid member having a central cylindrical portion. The cylindrical portion forms a hinge 1309 about which the rigid members 1305 and 1307 can freely pivot. In certain embodiments, the pivoting action is restricted to certain angular levels. In such an embodiment, the cylindrical portion comprises a range of different angular levels 1316. The angular levels 1316 allows a user to restrict the pivoting action of the rigid members to one or more of a select number of angular levels. The support system 1304 may be adapted to be set at one or more different angular levels and may be lockable and/or selectable.

Figure 11:
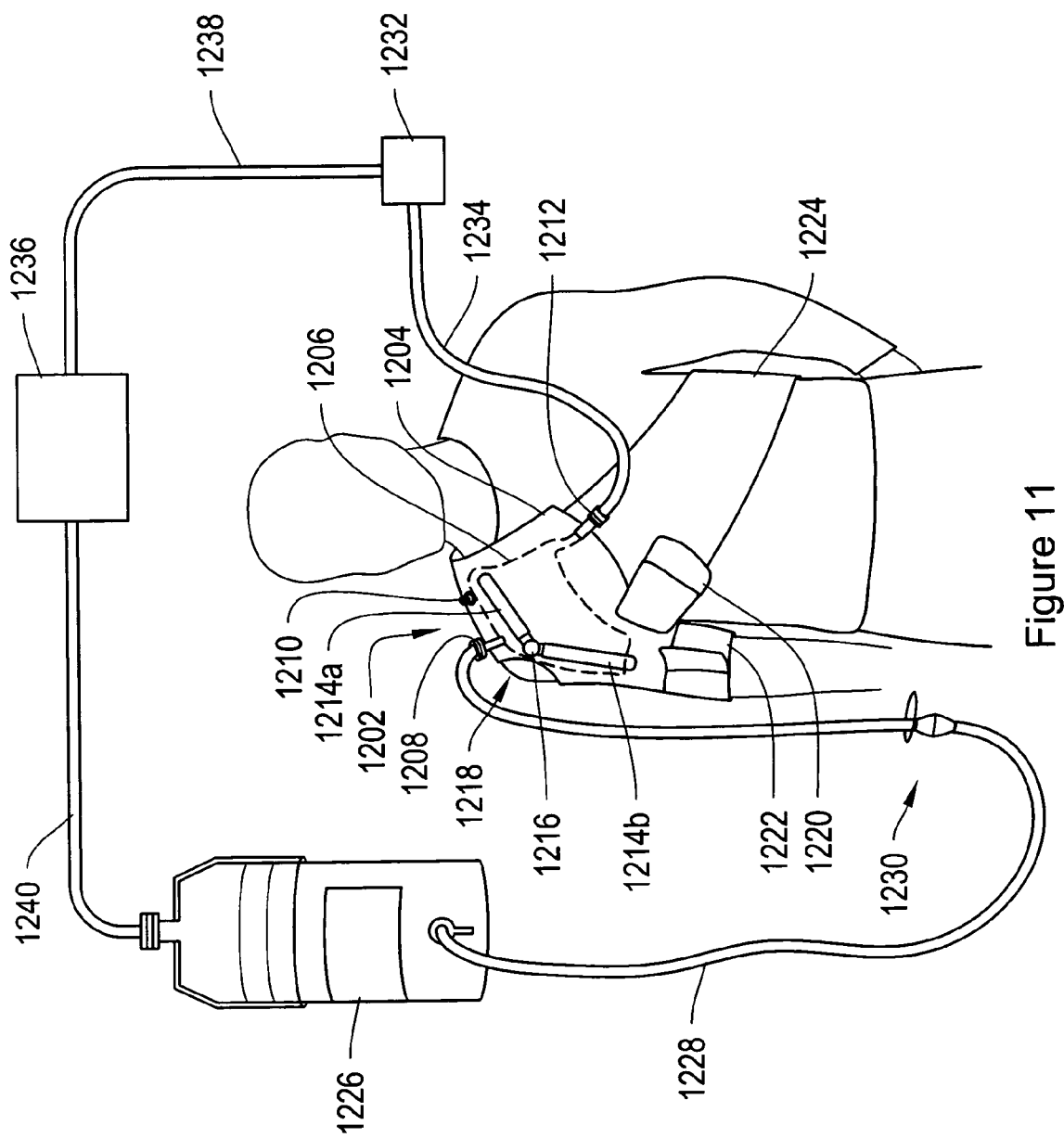
FIG. 11 depicts a temperature regulated compression system as applied to a patient's shoulder, according to an illustrative embodiment of the invention.

FIG. 11 depicts a temperature regulated compression system as applied to a shoulder of an individual, according to an illustrative embodiment of the invention. The system includes a brace 1202. The brace 1202 is similar to braces 100, 200 and 300 shown in FIGS. 1, 2A, 2B, and 3. Brace 1200 includes a shell 1204 having disposed thereon a fluid input port 1208, a fluid output port 1212 and an air release valve 1210. The brace 1202 includes a fluid compartment (shown in dotted lines), disposed within the shell 1204, in direct or indirect fluid communication with the fluid input port 1208, fluid output port 1212 and the air release valve 1210. The brace 1202 includes a support system having rigid members 1214a and 1214b (collectively, the "rigid member 1214") connected to each other at hinge 1216. The brace has a notch 1218 to accommodate the shoulder joint.

The brace 1202 includes a first strap 1222 and a second strap 1224 (collectively, the "straps 1222 and 1224") connected to the flexible shell 1204 and extending therefrom. The first strap 1222 is shown to be extending from the portion of the flexible shell 1204 on the arm of the individual. The first strap 1222 includes an attachment portion formed from suitable attaching materials such as VELCRO™. The brace 1202 is secured to the arm by wrapping the first strap 1222 around the arm and connecting the attachment portion. The second strap 1224 also includes an attachment portion 1220 formed from suitable attaching materials such as VELCRO™. The brace 1202 is secured around the shoulder of the individual by wrapping the second strap 1224 around the individual's torso, underneath the other arm and around the back. The second strap 1224 is connected to the attachment portion 1220 to snugly secure the brace 1202 to the individual's shoulder. In certain embodiments, the straps 1222 and 1224 are unitarily formed with the flexible shell 1204 and are adjustable. In such an embodiment, the individual slides the brace 1202 over the head and through the arm in a manner similar to wearing a t-shirt. The adjustable straps 1222 and 1224 allow for varying the tightness of the brace 1202.

The brace 1202 is in fluid communication with a fluid reservoir 1226, an optional pump 1232 and an optional heater/cooler 1236. As noted earlier, the brace 1202 includes a fluid input port 1208 and a fluid output port 1212, each in fluid communication with a fluid compartment 1206. A fluid conduit 1228 connects the fluid reservoir 1226 to the fluid compartments 1206 in the brace 1202 through fluid input port 1208. The fluid conduit 1228 is interrupted at valve 1230 configured to control fluid flow through the conduit 1228. Tubing 1234 and 1238 connects the heater/cooler 1236 to the fluid compartment 1206 through fluid output port 1212 and an optional pump 1232. Tubing 1240 connects the heater/cooler 1236 with the reservoir 1226.

In certain embodiments, temperature regulated fluid such as cold or hot water is stored in the reservoir 1226. During operation, fluid from the reservoir 1226 flows through the conduit 1228 and fluid input port 1208 into the fluid compartment 1206 of the brace 1202. The fluid output port 1212 may be temporarily closed to allow the fluid compartment 1206 to fill. In operation, as the fluid fills the fluid compartment 1206, it expands the brace 1202, compresses the shoulder and tightens the straps 1222 and 1224. In addition to compression, the brace 1202 provides for temperature treatment of the shoulder. In one embodiment, the temperature of the fluid is regulated to a high or low temperature to provide heat or cold therapy, respectively, to the shoulder joint.

In certain embodiments, the fluid warms or cools during treatment and therefore needs to be replaced. In such embodiments, at a desired time, the fluid output port 1212 is opened and the fluid input port 1208 is closed to allow the fluid in the fluid compartment 1206 to drain. The drained fluid passes through tubing 1234 and 1238 into a heater/cooler 1236. In certain optional embodiments, a pump 1232 is included in between the heater/cooler 1236 and the brace 1202 to facilitate the draining process. The heater/cooler 1236 heats and/or cools the drained fluid and replenishes the supply of temperature regulated fluid in the reservoir 1226 through tubing 1240.

In certain embodiments, fluid is supplied to the brace 1202 in an intermittent manner so as to provide periods of compression and de-compression. In certain embodiments, the fluid is supplied so that the periods are applied in an alternating fashion. In certain embodiments, the temperature of the fluids being supplied to the brace 1202 are changed in an alternating manner so as to iteratively provide periods of hot therapy and periods of cold therapy. In still other embodiments, the fluid is supplied to the brace 1202 in a steady continuous manner and the temperature is changed in an alternating manner so as to provide steady compression along with periods of hot and cold therapy. In such embodiments, the fluid input port 1208 and the fluid output port 1212 are kept open in partially overlapping intervals of time. Various combinations of hot, cold, compressive and decompressive therapy may be provided for varying intervals of time without departing from the scope of the invention.

In certain embodiments, the rigid members 1214 and hinge 1216 of the brace 1202 are configured to restrict movement of the shoulder about at least one of the acromioclavicular (AC) joint and the glenohumeral joint. In such embodiments, rigid members 1214 are positioned along at least one of the acromion, clavicle, humerus and glenoid bones. The rigid members 1214 and hinge 1216 may be applied so as to restrict movement along any ball and socket joint or spheroidal joint of the patient.

The features and structures described above with respect to any particular embodiment may be applied to any other embodiments disclosed herein. For example, the features of FIG. 11 may be applied to the systems depicted in FIGS. 1-10C without departing from the scope of the invention. In certain exemplary implementations, the braces of FIG. 1-10B are adapted to include one or more fluid ports for receiving fluid (e.g., port 1208) and one or more separate fluid ports for removing fluid (e.g., port 1212), with each of such ports configured with tubing systems to connect with external fluid sources or receptacles. In certain embodiments, the support system in one or more braces shown in FIGS. 1-11 may be configured to restrict movement along at least one of condyloid joint (e.g., wrist-joint), sellar joint (e.g., thumb) and trochoid joint. As described herein, the support system in one or more braces shown in FIGS. 1-11 may provide movement restrictions that include one or more of flexion, extension, adduction, abduction, elevation, depression, pronation, supination, dorsiflexion, plantarflexion, eversion and inversion about the applicable joint, While the invention has been shown and described with respect to particular embodiments thereof, this is for the purpose of illustration rather than limitation; other variations and modifications of the specific embodiment herein shown and described will be apparent to those skilled in the art, all within the intended spirit and scope of the invention. In particular, the systems and methods include devices to provide a thermal therapy, whether hot or cold temperature, or a combination of the two. The systems and methods described herein may be used to provide wrist wraps and braces, elbow wraps and braces, and wraps and braces that apply to the shoulder, neck or waist. The systems and methods may use cells that fill with water, gel, or other fluid, and may include multi-celled devices into which different fluids may be passed. The systems and methods may operate with a reservoir cooler, a reservoir pack, or may be filled from a faucet or other source of fluid.

Those skilled in the art will know or be able to ascertain using no more than routine experimentation, many equivalents to the embodiments and practices described herein. Accordingly, it will be understood that the invention is not to be limited to the embodiments disclosed herein, but exemplary embodiments are to be understood from the following claims, which are to be interpreted as broadly as allowed under the law. All references cited herein are hereby incorporated by reference and made a part of this application.

What is claimed is:

1. A bracing system for a human limb, comprising:
   a flexible shell configured to be removably secured about a limb,
   a fluid compartment formed within the flexible shell, the fluid compartment having a fluid input port for connecting to an external fluid source,
   two rigid members being removably coupled to the flexible shell for bracing the limb, and
   a hinge coupled to the rigid members for allowing a pivoting motion of the rigid members and therefore a controlled movement of the limb, and
   at least one of a heater or a cooler to regulate temperature of fluid in the external fluid source.

2. The bracing system of claim 1, comprising pockets attached to the flexible shell for housing the rigid members.

3. The bracing system of claim 2, wherein the rigid member are removably disposed within the pockets.

4. The bracing system of claim 1, wherein the fluid compartment is inflexible and is compressed against the limb by at least one strap.

5. The bracing system of claim 1, wherein the fluid compartment is flexible and adapted to compress the limb when fluid is placed therein.

6. The bracing system of claim 1, wherein the flexible shell comprises an aperture for receiving a portion of the limb.

7. The bracing system of claim 1, wherein the flexible shell is configured to support at least one of a knee, an elbow, an ankle, a spine, a shoulder and a wrist.

8. The bracing system of claim 1, comprising a plurality of straps.

9. The bracing system of claim 1, comprising at least one strap to secure the system about the limb.

10. The bracing system of claim 9, wherein the at least one strap includes a layer of foam attached thereto.

11. The bracing system of claim 1, comprising a separate closeable fluid output port in fluid communication with the at least one of the heater or the cooler.

12. The bracing system of claim 11, wherein the fluid input port and the separate fluid output port are kept open in partially overlapping intervals of time allowing the brace to provide a steady compression along with alternating periods of hot and cold therapy.

13. The bracing system of claim 11, comprising a pump connected to the at least one of the heater or the cooler and the fluid output port to facilitate a fluid draining process.

14. The bracing system of claim 1, wherein the fluid compartment is formed from a material capable of receiving at least one of a high temperature fluid and a low temperature fluid.

15. The bracing system of claim 1, wherein the fluid compartment is formed from a material capable of holding at least one of a high temperature thermal fluid and a low temperature thermal fluid.

16. The bracing system of claim 1, further comprising a siphon disposed within the flexible shell and in fluid communication with the fluid port and the fluid compartment.

17. The bracing system of claim 1, further comprising an air release valve in fluid communication with the fluid compartment.

18. The bracing system of claim 1, wherein the fluid compartment includes a layer of insulation.

19. The bracing system of claim 1, comprising a plurality of rigid members.

20. The bracing system of claim 19, comprising at least two rigid members disposed on lateral and medial portions of the limb.

21. The bracing system of claim 1, wherein the rigid members include at least one of metal, plastic and fiberglass.

22. The bracing system of claim 1, wherein the rigid members are joined at a pre-determined angle with respect to each other by the hinge.

23. The bracing system of claim 22, wherein the pre-determined angle is less than 180°.

24. The bracing system of claim 23, wherein the selectable hinge is configured to allow the rigid member to rotate from about 10 degrees to about 15 degrees.

25. The bracing system of claim 1, wherein the hinge includes a ratchet mechanism.

26. The bracing system of claim 1, comprising a fluid reservoir connected to a fluid port for providing fluid to the fluid compartment.

27. The bracing system of claim 26, wherein the fluid reservoir is connected to the fluid port using a removable valve.

28. The bracing system of claim 27, wherein the valve includes a one-way valve configured to allow fluid storage within the fluid compartment.

29. The bracing system of claim 1, wherein the fluid is supplied to the brace in an intermittent manner so as to provide periods of compression and de-compression.

30. A method of bracing a patient's limb, comprising
applying a fluid compartment about the limb,
applying at least one rigid member along at least one of lateral, medial, posterior and anterior sides of the limb, the rigid member being removably coupled to the fluid compartment and providing patient controlled pivotable movement of the braced limb, and
inserting a temperature regulated fluid into the fluid compartment to compress the limb while concomitantly bracing the limb by the at least one rigid member.

31. The method of claim 30, comprising the step of strapping the fluid compartment about the limb to compress the joint.

32. The method of claim 30, comprising the step of inserting cold fluid into the fluid compartment.

33. The method of claim 30, wherein the rigid member is hinged to form proximal and distal rigid members.

34. The method of claim 33, comprising controlling the movement of the proximal and distal rigid members by adjusting the angle of the hinge.

35. The method of claim 33, comprising the step of locking the hinge to position the rigid member at an angle that prevents the limb from hyper-extending.

36. The method of claim 30, comprising supporting the limb while the patient walks.

37. The method of claim 30, comprising introducing air into an outer compartment formed about the fluid compartment to compress the limb.

38. The method of claim 30, comprising positioning a portion of the limb within an aperture.

39. The method of claim 30, comprising the step of providing a fluid reservoir in communication with the fluid compartment such that the temperature regulated fluid is introduced from the fluid reservoir into the fluid compartment.

40. The method of claim 30, comprising the step of holding the temperature regulated fluid in the fluid compartment.

41. The method of claim 30, comprising the step of removing the temperature regulated fluid from the fluid compartment.

42. The method of claim 41, wherein the steps of introducing the temperature regulated fluid and removing fluid from the expandable fluid compartment are carried out iteratively thereby providing a continuous supply of temperature regulated fluid to a portion of the limb.

43. The method of claim 30, comprising the step of providing a fluid input port and a separate fluid output port in connection with the fluid compartment for introducing and removing, respectively, temperature regulated fluid.

44. The method of claim 43, wherein the fluid input port and the separate fluid output port are kept open in partially overlapping intervals of time allowing the brace to provide a steady compression along with alternating periods of hot and cold therapy.

45. The method of claim 30, wherein the fluid is supplied to the brace in an intermittent manner so as to provide periods of compression and de-compression.

46. A bracing system for a human limb, comprising:
a flexible shell configured to be removably secured about a limb,
a fluid compartment formed within the flexible shell, the fluid compartment having a fluid input port for connecting to an external fluid source and a separate fluid output port,
a rigid member being coupled to the flexible shell for bracing the limb and providing patient controlled pivotable movement of the braced limb, and
at least one of a heater or a cooler to regulate temperature of fluid in the external fluid source.

47. The bracing system of claim 46, wherein the separate fluid output port is in fluid communication with the at least one of the heater or the cooler.

48. The bracing system of claim 46, wherein the fluid compartment is inflexible and is compressed against the limb by a least one strap.

49. The bracing system of claim 46, wherein the fluid compartment is flexible and adapted to compress the limb when fluid is placed therein.

50. The bracing system of claim 46, wherein the flexible shell comprises an aperture for receiving a portion of the limb.

51. The bracing system of claim 46, wherein the flexible shell is configured to support at least one of a knee, an elbow, an ankle, a spine, shoulder and a wrist.

52. The bracing system of claim 46, comprising at least one strap to secure the system about the limb.

53. The bracing system of claim 52, wherein the at least one strap includes a layer of foam attached thereto.

54. The bracing system of claim 46, further comprising an air release valve in fluid communication with the fluid compartment.

55. The bracing system of claim 46, wherein the fluid compartment includes a layer of insulation.

56. The bracing system of claim 46, wherein the rigid member includes at least one of metal, plastic and fiberglass.

* * * * *

UNITED STATES PATENT AND TRADEMARK OFFICE
CERTIFICATE OF CORRECTION

PATENT NO. : 7,744,551 B2
APPLICATION NO. : 11/493152
DATED : June 29, 2010
INVENTOR(S) : Pick et al.

It is certified that error appears in the above-identified patent and that said Letters Patent is hereby corrected as shown below:

Column 16, Claim 3, Line 55, replace "member" with --members--

Signed and Sealed this

Second Day of November, 2010

David J. Kappos
*Director of the United States Patent and Trademark Office*